United States Patent [19]

Antrim et al.

[11] 4,355,117

[45] Oct. 19, 1982

[54] PROCESS FOR PREPARING AGGLOMERATED FIBROUS CELLULOSE

[75] Inventors: Richard L. Antrim; Louis S. Hurst, both of Clinton, Iowa

[73] Assignee: Nabisco Brands, Inc., New York, N.Y.

[21] Appl. No.: 195,214

[22] Filed: Oct. 8, 1980

[51] Int. Cl.$^3$ .................. C08B 5/14; C08B 11/145; B01J 39/22; B01J 41/16

[52] U.S. Cl. .................................... 521/28; 521/32; 260/17 R

[58] Field of Search .................. 260/17 R; 521/28, 32

[56] References Cited

U.S. PATENT DOCUMENTS

| | | | |
|---|---|---|---|
| 3,083,118 | 3/1963 | Bridgeford | 521/28 |
| 3,597,146 | 8/1971 | Tesoro | 521/30 |
| 3,652,540 | 3/1972 | Petermann | 521/30 |
| 3,708,397 | 1/1978 | Sipos | 195/31 R |
| 3,788,945 | 1/1974 | Thompson et al. | 195/31 F |
| 3,823,133 | 7/1974 | Hurst et al. | 195/31 R |
| 3,838,007 | 9/1974 | van Velzen | 195/31 F |
| 3,909,354 | 9/1975 | Thompson et al. | 195/31 F |
| 3,947,325 | 3/1976 | Dinelli et al. | 195/68 |
| 3,956,065 | 5/1976 | Idaszak et al. | 195/31 F |
| 4,110,164 | 8/1978 | Sutthoff et al. | 195/62 |
| 4,168,250 | 9/1979 | Sutthoff et al. | 260/17.4 |

FOREIGN PATENT DOCUMENTS 938743 10/1963 United Kingdom .................. 521/28

OTHER PUBLICATIONS

E. A. Peterson & H. A. Sober. "Chromatography of Proteins, I. Cellulose Ion-exchange Adsorbents." *J.A.C.S.*, vol. 78, pp. 751–755 (1956).

J. D. Guthrie & A. L. Bullock. "Ion Exchange Celluloses for Chromatographic Separations."*Industrial and Engineering Chemistry*, vol. 52, No. 11, pp. 935–937 (1960).

N. Tsumura & M. Ishikawa. "A Continuous Glucose Isomerization Method by an Adsorbed Enzyme Column."*Nippon Shokuhim Kogyo Gakkaishi*, vol. 14, No. 12 (1967).

J. Peska, et al. "Chemical Transformation of Polymers; XIX. Ion Exchange Derivatives of Bead Cellulose."*Die Angewandte Makromolekulare Chemie*, vol. 53, No. 786, pp. 73–80 (1976).

*Primary Examiner*—William F. Hamrock
*Assistant Examiner*—Peter F. Kulkosky
*Attorney, Agent, or Firm*—Richard Kornutik; Henry S. Wyzan; Robert A. Conzett

[57] ABSTRACT

A process is provided wherein a fibrous ion exchange cellulose composite is prepared by agglomerating a hydrophobic polymer and fibrous cellulose and then derivatizing the cellulose to impart ion exchange properties thereto. The process is an improvement over the prior art processes wherein the composite is prepared by agglomerating the polymer with fibrous cellulose which has been converted to ion exchange cellulose prior to agglomeration.

28 Claims, No Drawings

PROCESS FOR PREPARING AGGLOMERATED FIBROUS CELLULOSE

BACKGROUND OF THE INVENTION

This invention relates to an improved process for preparing agglomerated fibrous ion exchange cellulose composites. More particularly, this invention relates to a more efficient process for preparing such composites having greater ion exchange capacity than those prepared by prior art methods.

In food processing and other commercial applications the use of microbial or fungal enzymes adsorbed onto or bonded to inert carriers to provide immobilized biological catalysts has largely superseded older methods wherein soluble enzymes or whole cells of microorganisms were utilized. In general, the use of immobilized enzymes provides a number of significant advantages over the older methods. The major advantage is that the immobilized enzymes are adaptable for use in continuous conversion processes. Thus, a more efficient use of the enzyme is attained and the contact time between the enzyme and the substrate is reduced, thereby resulting in an improved product quality and a reduction in enzyme and production costs.

Although the following description and Examples are primarily directed to the utilization of agglomerated fibrous ion exchange cellulose to adsorb and immobilize glucose isomerase, it is contemplated that the agglomerated material will have the capability of adsorbing other enzymes, charged macro-molecules such as other proteins, nucleic acids and the like, and, further, would be capable of recovery of said molecules from a variety of substances such as food waste streams, e.g. recovery of protein from milk whey, meat processing streams and vegetable processing streams, reduction of BOD from waste streams, etc.

Because of the economics involved in producing glucose isomerase, it is of the utmost importance to use the isomerase under conditions whereby maximum yields of fructose are produced using minimum quantities of the enzyme. Moreover, the conditions for isomerization should be such that minimal quantities of objectionable by-products are produced.

In recent years, more economical methods for producing fructose-containing solutions have been developed utilizing glucose isomerase bound or immobilized on inert support materials. Such materials include various polymeric substances such as derivatized cellulose, ion exchange resins and synthetic fibers, glass, insoluble organic and inorganic compounds, etc. Glucose isomerase has also been encapsulated or englobed in suitable materials but such preparations suffer from the disadvantage that they generally cannot be reused.

THE PRIOR ART

Cellulose occurs in nature as a linear polymer comprised of anhydroglucose units joined together by $\beta$-1,4 glucosidic bonds. Each anhydroglucose unit contains three free hydroxyl groups capable of reacting with appropriate reagents to form insoluble cellulose derivatives which, due to their relative inertness, large surface area and open, porous structure, have a high adsorptive or ion-exchange capacity for protein molecules.

The preparation and utilization of ion exchange enzyme adsorbents derived from cellulose are known in the art. Peterson and Sober, *J.A.C.S.* 78, 751 (1956) and Guthrie and Bullock, *I/EC,* 52, 935 (1960) described methods for preparing adsorptive cellulose products which could be utilized to separate or purify enzymes and other proteins. Tsumura et al., *Nippon Shokuhin Kogyo Gakkaishi,* 14, (12), (1967) disclosed binding glucose isomerase to DEAE-Sephadex.

U.S. Pat. No. 3,708,397 to Sipos relates to a process for immobilizing glucose isomerase on basic anion exchange celluloses. U.S. Pat. No. 3,823,133 to Hurst et al. is directed to a method for preparing cationic cellulose ethers having a high adsorptive capacity for enzymes and other proteinaceous materials. U.S. Pat. No. 3,838,007 to van Velzen sets forth a process in which an enzyme preparation is obtained in particulate form. U.S. Pat. Nos. 3,788,945 and 3,909,354, both to Thompson et al., disclose continuous processes for converting glucose to fructose by passing a glucose-containing solution through fixed or fluidized beds containing glucose isomerase bound to various cellulose products. U.S. Pat. No. 3,947,325 to Dinelli et al. is directed to the preparation of cellulose-containing englobed enzymatic material. The cellulose is formed from an emulsion comprising an aqueous enzyme solution and nitrocellulose. U.S. Pat. No. 3,956,065 to Idaszat et al. is concerned with a continuous process for converting glucose to fructose whereby a glucose-containing solution is passed through a bed comprising a cellulose derivative having glucose isomerase immobilized thereon and non-porous or granular polystyrene beads. The beads inhibit packing and channeling of the bed when such is used in flow reactors. Peska et al. in an article entitled "Ion Exchange Derivatives of Bead Cellulose," *Die Angewandte Makromolekulare Chemie,* 53, pp. 73-80 (1976), describes several derivatized celluloses prepared in bead form.

U.S. Pat. Nos. 4,110,164 and 4,168,250 both to Sutthoff et al. relate to agglomerated fibrous ion exchange cellulose composites and processes for preparing the same. In these processes a hydrophobic polymer is combined with fibrous cellulose which has previously been derivatized to impart ion exchange properties thereto. Although these composites perform satisfactorily in a number of applications, their ion exchange capability and capacity for adsorbing or binding glucose isomerase are not as great as desired. Moreover, the economics of these processes are such as to make the production of the composites more costly than is preferred.

OBJECTS OF THE INVENTION

It is a principal object of the present invention to provide an improved process for preparing agglomerated fibrous ion exchange cellulose composites capable of adsorbing and immobilizing charged macro-molecules.

It is another object of the present invention to provide an improved process for preparing agglomerated fibrous ion exchange cellulose composites having good porosity characteristics in respect to the flow therethrough of a solution of a substrate when such composite is used as an immobilized enzyme support.

It is yet another object of the present invention to provide an economical process for preparing agglomerated fibrous ion exchange cellulose composites.

These and other objects and advantages of the invention will be apparent from the present specification and the appended claims.

SUMMARY OF THE INVENTION

An improved process is provided for preparing an agglomerated fibrous ion exchange cellulose composite wherein relatively large portions of the cellulose are free to adsorb charged macro-molecules. An agglomerate is formed comprising fibrous cellulose and a hydrophobic polymer following which the cellulose is derivatized to impart ion exchange properties thereto.

DETAILED DESCRIPTION OF THE INVENTION

The term "fibrous" as used in this specification and the appended claims refers to cellulose derived from natural sources which has been subdivided or fiberized by mechanical or chemical means and does not include cellulose or derivatives thereof which have been subjected to chemical treatments which result in dissolution of the natural fibrous structure of the cellulose such as may occur when cellulose is derivatized to high degrees of substitution.

Fibrous cellulose can be derivatized to provide ion exchange materials having high loading capacities in regard to adsorbing or immobilizing macro-molecules. For this purpose, the cellulose may be derivatized to provide ion exchange materials having either anion or cation exchange capabilities, depending upon the charge present on the material to be adsorbed. When the material to be adsorbed is glucose isomerase, the cellulose will advantageously be derivatized to the anion exchange form since in this form its loading capacity for this enzyme is extremely high. Typically, to produce the anion exchange form, the agglomerated fibrous cellulose will be treated with appropriate reagents to form, among others, the di- and tri-ethylaminoethyl celluloses, such as DEAE-cellulose and TEAE-cellulose, and the cellulose derivatives of epichlorohydrin and triethanolamine, such as ECTEOLA-cellulose. Background information and methods for derivatizing cellulose are disclosed in U.S. Pat. No. 3,823,133 to Hurst et al.

Due to the high loading capacity of fibrous ion exchange cellulose preparations containing glucose isomerase, when such are utilized in industrial applications, relatively small reactors may be employed to convert large quantities of glucose to fructose.

Additionally, because of this high loading capacity, the substrate and the resulting product are maintained under isomerization conditions for only a short period. These isomerization conditions, generally, are conducive to production of small amounts of unwanted by-products due to the reactive nature of the fructose, and, thus, the longer the period the fructose is maintained under such conditions, the greater the amounts of unwanted by-products produced. Thus, the high loading capacity of fibrous ion exchange cellulose results in the substrate being isomerized to the desired degree in a short time, thereby decreasing the period during which the fructose component is maintained under isomerization conditions. However, such preparations containing fibrous ion exchange cellulose suffer from the disadvantage of "packing" and, therefore, such are usually utilized in shallow beds to avoid the development of problems due to excessive backpressure. Even when shallow beds are utilized, there is the possibility of channeling occurring whereby the substrate is not contacted to the desired degree with the bound or immobilized glucose isomerase. Although certain immobilized glucose isomerase preparations have been developed to minimize these problems, they generally suffer other disadvantages, e.g., their enzyme capacity or activity per unit volume is not as high as is desired, and/or they are not as economical as fibrous ion exchange cellulose.

In practicing the present invention a number of polymers may be utilized to agglomerate the fibrous cellulose. Exemplary of such as melamine formaldehyde resins, epoxy resins, polystyrene and the like. The preferred polymer is polystyrene.

In U.S. Pat. Nos. 4,110,164 and 4,168,250 it is disclosed that when fibrous cellulose which has been derivatized to provide an ion exchange material is agglomerated with a hydrophobic polymer under suitable conditions, such cellulose retains its capacity to immobilize or bind glucose isomerase. The preferred process taught for preparing the composites comprises treating alkali-cellulose with a solution of diethylaminoethyl chloride hydrochloride (DEC) and then agglomerating the derivatized ion exchange cellulose formed thereby with polystyrene. Due to the solubility of polystyrene in the DEC reaction mixture, however, it would be anticipated that the cellulose could not be efficiently derivatized if the agglomerates were formed prior to derivatization of the cellulose.

We have surprisingly discovered that fibrous cellulose can be efficiently derivatized in the presence of the hydrophobic polymer by controlling process conditions during derizatization so as to prevent the polymer from becoming solubilized in the derivatizing solution. Thus, it has been found that by adding the derivatizing material at a controlled rate to a water suspension of the agglomerate under alkaline conditions, the hydrophobic polymer component of the granular composite does not become solubilized to a significant degree.

A further unexpected finding is that when the cellulose is derivatized following agglomeration thereof, the cellulose composite may be derivatized to a higher degree and thus have a greater ion exchange capacity than the agglomerated cellulose composite produced by the process of the prior art, wherein the cellulose is derivatized before agglomerization. While the ion exchange capacity of the agglomerated fibrous cellulose composite of this invention may vary widely, typically the ion exchange capacity should be at least about 0.1 meq $g^{-1}$ and preferably at least about 0.2 meq $g^{-1}$.

The agglomerated fibrous ion exchange cellulose composites of this invention may also be regenerated; that is, after the activity of the immobilized glucose isomerase has decreased to a certain extent due to denaturation or other factors resulting from prolonged use, a solution of solubilized glucose isomerase can be brought into contact with a bed or column of the composite so that the glucose isomerase activity thereof is increased again to the desired degree. Prior to regeneration, however, it is generally preferred to treat the composite with a solution of alkali to make the ion exchange sites of the fibrous cellulose more readily available to isomerase adsorption. While we do not wish to be bound to any theory in regard to the mechanism involved, it is likely that substrate debris, denatured isomerase or other proteinaceous materials which have become attracted to the fibrous cellulose are removed or solubilized.

When fibrous cellulose is derivatized prior to agglomeration, the materials used in the derivatization reaction tend to cause the cellulose to swell or become partially solubilized and difficult to recover by filtration. Recovery of the composite of the present invention is simplified by the fact that such swelling as may occur does not present a serious filtration problem due to the granular nature of the derivatized product. Additionally, since the granular cellulose composites do not suffer from serious packing problems, they can be utilized in deep bed reactors without difficulty and with a minimum of channeling occurring.

Depending upon the specific gravity of the substrate, the agglomerated fibrous ion exchange cellulose composite may tend to float thereon and, therefore, there is the possibility of some loss of composite occurring through the inlet or outlet portions of column type reactors. Moreover, problems could occur when the column is initially packed with the composite. Therefore, in certain cases, it is preferred to incorporate a densification agent into the agglomerated fibrous ion exchange cellulose composite to increase the density thereof.

While a variety of densification agents may be utilized, they must, of course, be substantially inert in regard to the substrate and also must not inactivate the glucose isomerase. Densification agents such as powdered metal oxides or silicates or mixtures thereof may be utilized.

To form the agglomerated fibrous composite, the fibrous cellulose must be embedded in the hydrophobic polymer in such a manner that the cellulose is not completely encapsulated or enrobed in the polymer. Otherwise, the capacity of the fibrous ion exchange cellulose to adsorb enzymes would be deleteriously affected. The greater the free surface of the cellulose, the greater the adsorptive capacity of the composite.

While a number of methods may be utilized to embed the fibrous cellulose in the hydrophobic polymer, the two which may be typically used involve dissolving the hydrophobic polymer in an organic solvent and incorporating the other materials therein, or heating the polymer to a plastic state and incorporating the other materials. The latter procedure is preferred since no solvent evaporation is necessary. The resulting material can then be reduced by grinding or the like, the granules classified on appropriate sized screens, and the agglomerated fibrous cellulose derivatized.

The particle size distribution of the granules may vary somewhat widely. Satisfactory results have been obtained using granules which passed through No. 20 and were retained on No. 60 U.S. mesh screens.

In order to more clearly describe the nature of the present invention, specific examples will hereinafter be described. It should be understood, however, that this is done solely by way of example and is intended neither to delineate the scope of the invention nor limit the ambit of the appended claims.

EXAMPLE I

This example illustrates the process for preparing an agglomerated fibrous ion exchange cellulose composite whereby the cellulose component of the composite is derivatized after agglomeration.

An agglomerate was prepared by mixing 25 parts of chemical grade cellulose (C-100, manufactured by International Filler Corp., North Tonawanda, N.Y.) with 25 parts of alumina and compounding the mixture with 50 parts of polystyrene on a heated (180°-200° C.) twin roll compounder for a period of about 10 minutes. After cooling, the compounded composite was ground and sized to 40-100 mesh.

220 grams of the sized composite was slurried in 616 ml of water containing 176 grams of $Na_2SO_4$ and 26.4 grams of NaOH. The slurry was heated to 40° C. following which 57.2 grams of a 50 percent aqueous solution of DEC was metered into the slurry with stirring at a rate of 0.7 ml $min^{-1}$ over a period of about one hour. Next, another 26.4 grams of NaOH dissolved in 26 ml of water was added to the slurry followed by an additional 57.2 grams of the DEC solution at 0.7 ml $min.^{-1}$.

The temperature of the slurry was then raised to 60° C. and held at this temperature for 15 minutes. A volume of water approximately equal to the volume of the slurry was added and the composite recovered on a 60 mesh screen. The composite was washed on the screen with water and reslurried in a volume of water similar to that added previously. This slurry was adjusted to a pH of about 7 with HCl, washed and dewatered on filter paper and dried.

The ion exchange capacity of the dried product was determined to be 0.84 meq $g^{-1}$ on a cellulose basis and 0.21 meq $g^{-1}$ on the basis of the agglomerated composite.

The ion exchange capacity of the composite was determined by the following procedure:

1. Weigh 20 g d.b. of derivatized agglomerated cellulose (5-10 g cellulose basis).
2. Slurry in water and adjust the pH to 12.5-13.0 with 1-N NaOH.
3. Wash the slurry into a chromatography column and place a porous disk on top of bed.
4. Add approximately 10 ml of 1-N NaOH to column and drain dropwise to disk level, rinse column with wash bottle and drain to disk.
5. Wash with approximately 6 bed volumes of water using approximately 2 bed volumes per rinse. Allow head to drain down to top of disk for each rinse.
6. Add 25 ml of 1-N HCl to top of bed and rinse down with about 10 ml of water from wash bottle. Start fresh collection of effluent, dropwise, at about 1-1.5 ml/min. Rinse down with wash bottle as head level reaches disk.
7. Wash with approximately 6 bed volumes as in Step 5.
8. Titrate the effluent to pH 7.0 with 1-N NaOH. The ion exchange capacity was calculated as follows:

I.E. Capacity (meq $g^{-1}$, $d.b.$) =

$$\frac{(ml\ HCL \times N) - (ml\ NaOH \times N)}{gms\ adsorbent,\ d.b.}$$

In Example I it can be calculated that the ratio of derivatizing agent (DEC) to cellulose was 1.04 on a dry weight basis whereas in the prior art method described in U.S. Pat. No. 4,110,164 the cellulose was derivatized before agglomeration at a DEC to cellulose ratio of 0.7. This value represents approximately the maximum extent to which non-agglomerated cellulose can be derivatized and recovered without difficulty by by conventional means.

EXAMPLE II

This example illustrates the process for preparing an agglomerated fibrous ion exchange cellulose composite wherein the cellulose is derivatized after agglomeration at a DEC to cellulose ratio of greater than two.

An agglomerated composite, prepared as shown in Example I, was ground and sized to 40 to 80 mesh. 100 grams of the sized composite was slurried in 280 ml of water in which had been dissolved 80 grams of $Na_2SO_4$ and 24 grams of NaOH. With the slurry at a temperature of 40° C., 55 grams of a 50 percent DEC solution was metered thereinto with stirring at a rate of 0.5 ml $min^{-1}$ over a period of about 1.5 hours. Additional NaOH (26 grams of a 50 percent solution) was then added to the slurry and an additional 55 grams of the DEC solution was metered into the slurry as in the first addition. The reaction mixture was heated to 60° C. and held at this temperature for 15 minutes. A volume of water equal to the slurry volume was added and the diluted slurry dewatered and washed on a 60 mesh screen. The product was reslurried in water, adjusted to a pH of from about 6.5 to 7.0 with HCL and screened and washed as above.

The ion exchange capacity of the dried composite was determined by the method shown above to be 1.28 meq $g^{-1}$ on a cellulose basis and 0.32 meq $g^{-1}$ on a composite basis. To achieve a comparable ion exchange capacity using the prior art method whereby derivatized DEAE-cellulose is agglomerated with polystyrene would require a degree of derivatization such as to render the cellulose gelatinous and difficult to recover, filter and dry without expensive treatments such as the use of a solvent or salt solutions or crosslinking the cellulose.

EXAMPLE III

This example illustrates the adsorptive capacity for glucose isomerase of the agglomerated fibrous ion exchange cellulose composites hereinabove described and the composites described in the prior art and provides a comparison of the characteristics and functional properties of said composites.

Glucose isomerase derived from microorganisms of a Streptomyces species, and having a potency of about 20 IGIU $ml^{-1}$ was added to equal weights of the composites prepared by the processes described in U.S. Pat. No. 4,110,164 and in Examples I and II above. The enzyme/composite slurries were adjusted to pH 7 and stirred for 5 hours at a temperature of 25° C. The composites were recovered by filtration and the amount of the enzyme adsorbed thereon determined by measuring the residual glucose isomerase activity in the respective filtrates by the method described by N. E. Lloyd et al. in *Cereal Chem.*, Vol. 49(5), p. 544, 1972.

The amounts of glucose isomerase adsorbed by the individual composites and data illustrating certain functional characteristics of the same are set forth in Table I.

TABLE I

| Composite | Ratio (wt/wt) DEC:Cellulose | Ion Exchange Capacity (meq g-1) | Adsorptive Capacity (IGIU g-1) |
|---|---|---|---|
| Example I | 1.04 | 0.21 | 490 |
| Example II | 2.2 | 0.32 | 690 |
| U.S. Pat. No. 4,110,164 | 0.7 | 0.14 | 361 |

EXAMPLE IV

This example illustrates the porosity characteristics of agglomerated fibrous ion exchange cellulose composites prepared by the present process and compares the flow properties of said composites with those of a prior art composite and of certain unagglomerated fibrous cellulose products.

The porosity characteristics of the following materials were determined:

1. a&b. Crosslinked Whatman celluloses manufactured by W & R Balston Ltd., England.
2. Non-crosslinked DEAE-cellulose (prepared as described in U.S. Pat. No. 3,823,133).
3. Composite prepared by agglomerating fibrous ion exchange cellulose and polystyrene (prepared as described in U.S. Pat. No. 4,110,164).
4. Composite prepared in Example I, above.
5. Composite prepared in Example II, above.

A porosity constant was determined for each of the above materials by the following procedure:

15 to 75 grams of dry product was slurried in water and the slurry deaerated by stirring under vacuum for 15 minutes. A glass column (1.5 inches inside diameter, 18 inches high) fitted with a porous glass disc and a stopcock at the bottom was attached to a vacuum flask through a rubber stopper. The flask was in turn attached to a vacuum source. The deaerated slurry was poured into the column and a vacuum (12.3 p.s.i. below atmospheric pressure) was applied to the bottom of the column by opening the stopcock, thereby forming a bed of the material on the porous glass disk. Simultaneously, water was admitted at the top of the column to replace that removed by filtration so that about 5 inches of water was maintained above the bed at all times. When a total of 1,000 ml of water had been collected, the stopcock was closed, the flask removed and the water emptied from the flask. The flask was then reattached to the column, the vacuum reestablished, the stopcock opened and a measured quantity (1,000 to 3,000 ml) of water was filtered through the packed bed and collected. The time required to collect the water was determined with a stop watch. The porosity constant was calculated using the following equation:

$$K = (VH)/(TPA)$$

Where:
K = porosity constant (ml cm $g^{-1}$ $min^{-1}$)
V = volume of water collected (ml)
H = height of packed bed (cm)
T = time to collect the water (min)
P = pressure drop across bed (g per square cm)
A = cross section of bed (square cm)
The results are shown in Table II.

TABLE II

| Material | Porosity Constant[1] (ml cm g-1 min-1) |
|---|---|
| 1 (a) | <0.21 |
| 1 (b) | 0.60 |
| 2 | 0.01 |
| 3 | 4.7 |
| 4 | 2.6 |
| 5 | 3.6 |

[1]a porosity constant of at least 1.5 ml cm g-1 min-1 is considered necessary for satisfactory performance in a deep bed reactor.

The terms and expressions which have been employed herein are used by way of description and not of limitation since it is not intended by the use of said terms and expressions to exclude any equivalents of the features shown and described or portions thereof and since it is recognized that various modifications are possible within the scope of the claimed invention.

What is claimed is:

1. In a process for preparing an agglomerated fibrous ion exchange cellulose composite capable of adsorbing or binding charged macro-molecules wherein a fibrous cellulose having ion exchange properties is agglomerated with a hydrophobic polymer, the improvement comprising first agglomerating a fibrous cellulose with a hydrophobic polymer to form a granular composite and then derivatizing the agglomerated fibrous cellulose in the composite at a ratio of derivatizing agent to cellulose of greater than 0.7" has been added after, to impart ion exchange properties thereto, at least portions of the derivatized cellulose being free to adsorb charged macro-molecules, and maintaining the composite in granular form.

2. A process according to claim 1, wherein the agglomerated cellulose is derivatized to impart anion exchange properties thereto.

3. A process according to claim 2, wherein the derivatized cellulose formed is DEAE-cellulose.

4. A process according to claim 3, wherein the hydrophobic polymer is polystyrene.

5. A process according to claim 1, wherein the composite has present a densification agent.

6. A process according to claim 5, wherein the densification agent is selected from the group consisting of powdered metal oxides, silicates and mixtures thereof.

7. A process according to claim 1, wherein the agglomerate is prepared by compounding the cellulose with the polymer which has been heated to a plastic state.

8. A process to claim 1, wherein the agglomerate is prepared by forming a solution of the polymer is an organic solvent and then incorporating the cellulose therein.

9. A process according to claim 1, wherein the composite is reduced to a particle size such that granules thereof will pass through a 20 mesh screen and be retained on a 60 mesh screen.

10. A process according to claim 1, wherein the hydrophobic polymer is selected from the group consisting of melamine formaldehyde resins, epoxy resins, polystyrene and mixtures thereof.

11. A process according to claim 1, wherein the ion exchange capacity of the composite is at least about 0.10 meq $g^{-1}$ on the basis of the dried ion exchange cellulose composite.

12. A process according to claim 1, wherein the ion exchange capacity of the composite is at least about 0.20 meq $g^{-1}$ on the basis of the dried ion exchange cellulose composite.

13. A process for preparing an agglomerated fibrous ion exchange cellulose composite comprising first embedding fibrous cellulose in a hydrophobic polymer and forming therefrom a granular composite treating the composite at a ratio of derivatizing agent to cellulose of greater than 0.7" has been added after, under conditions whereby the cellulose therein is derivatized to impart ion exchange properties thereto, and recovering a granular product wherein at least portions of the derivatized cellulose are free to adsorb charged macro-molecules.

14. A process according to claim 13, wherein the cellulose in the composite is derivatized to impart anion exchange properties thereto.

15. A process according to claim 14, wherein the derivatized cellulose formed is DEAE-cellulose.

16. A process according to claim 15, wherein the hydrophobic polymer is polystyrene.

17. A process according to claim 16, wherein the composite has present a densification agent.

18. A process according to claim 17, wherein the densification agent is selected from the group consisting of powdered metal oxides, silicates and mixtures thereof.

19. A process according to claim 1 or 13, wherein the macro-molecule is an enzyme.

20. A process according to claim 19, wherein the enzyme is glucose isomerase.

21. In a process for preparing an agglomerated fibrous ion exchange cellulose composite capable of absorbing or binding enzymes wherein a fibrous cellulose having ion exchange properties is agglomerated with a hydrophobic polymer, the improvement comprising first agglomerating a fibrous cellulose with a hydrophobic polymer to form a granular composite and then derivatizing the agglomerated fibrous cellulose in the composite at a ratio of derivatizing agent to cellulose of greater than 0.7" has been added after to impart ion exchange properties thereto, at least portions of the derivatized cellulose being free to adsorb enzymes, and maintaining the composite in granular form.

22. A process for preparing an agglomerated fibrous ion exchange cellulose composite comprising first embedding fibrous cellulose in a hydrophobic polymer and forming therefrom a granular composite treating the composite at a ratio of derivatizing agent to cellulose of greater than 0.7" has been added after, under conditions whereby the cellulose therein is derivatized to impart ion exchange properties thereto, and recovering a granular product wherein at least portions of the derivatized cellulose are free to adsorb enzymes.

23. A process according to claims 21 or 22, wherein the enzyme is glucose isomerase.

24. A process according to claim 23, wherein the agglomerated cellulose is derivatized to impart anion exchange properties thereto.

25. A process according to claim 24, wherein the hydrophobic polymer is selected from the group consisting of melamine formaldehyde resins, epoxy resins, polystyrene and mixtures thereof.

26. A process according to claim 25, wherein the hydrophobic polymer is polystyrene.

27. A process according to claim 26, wherein the ion exchange capacity of the composite is at least about 0.10 meq. $g^{-1}$ on the basis of the dried ion exchange cellulose composite.

28. A process according to claim 27, wherein the ion exchange capacity of the composite is at least about 0.20 meq. $g^{-1}$ on the basis of the dried ion exchange cellulose composite.

* * * * *

UNITED STATES PATENT AND TRADEMARK OFFICE
CERTIFICATE OF CORRECTION

PATENT NO. : 4,355,117
DATED : Oct. 19, 1982
INVENTOR(S) : Richard L. Antrim, et al It is certified that error appears in the above—identified patent and that said Letters Patent is hereby corrected as shown below:

Column 9, claim 1, line 10, after "0.7"" delete --has been added after,--.

Column 9, claim 13, line 59, after "0.7"" delete --has been added after,--.

Column 10, claim 21, line 29, after "0.7"" delete --has been added after--.

Column 10, claim 22, line 38, after "0.7"" delete --has been added after,--.

Signed and Sealed this

Fifth Day of April 1983

[SEAL]

Attest:

GERALD J. MOSSINGHOFF

Attesting Officer   Commissioner of Patents and Trademarks